United States Patent [19]
Corris

[11] 3,990,848
[45] Nov. 9, 1976

[54] SYSTEM FOR INDUCING AIR FLOW PAST A GEL TYPE PRODUCT

[75] Inventor: Charles James Corris, Camden, S.C.

[73] Assignee: The Risdon Manufacturing Company, Naugatuck, Conn.

[22] Filed: Apr. 10, 1975

[21] Appl. No.: 566,960

[52] U.S. Cl. ..................... 21/126; 21/55; 21/74 R; 21/77; 21/109; 239/57; 239/145
[51] Int. Cl.² ................... A61L 9/01; A61L 9/04
[58] Field of Search ............... 21/53, 55, 74 R, 77, 21/108, 109, 121, 122, 126; 239/57, 60, 145; 261/26, 30, 96, DIG. 17

[56] References Cited
UNITED STATES PATENTS

| | | | |
|---|---|---|---|
| 2,510,126 | 6/1950 | Melcher et al. | 21/126 |
| 2,614,820 | 10/1952 | Boydjieff | 21/126 |
| 2,629,149 | 2/1953 | Yaffe | 21/126 |
| 3,522,935 | 8/1970 | Lewis | 239/60 |
| 3,617,214 | 11/1971 | Dolac | 21/77 |
| 3,739,944 | 6/1973 | Rogerson | 239/70 |

*Primary Examiner*—Norman Yudkoff
*Assistant Examiner*—Dale Lovercheck
*Attorney, Agent, or Firm*—St. Onge Mayers Steward & Reens

[57] ABSTRACT

A system, which induces air flow past a gel type product and into the environment, comprises a cartridge that includes a porous container for holding the product and a battery mounted with the container. The cartridge is formed to be received in an air flow inducing device that includes a housing having an air admitting opening and an air discharging opening. A fan is mounted in the housing to induct air flow through the air admitting opening, through the container, past the product and out of the air discharging opening into the environment. The fan is driven by a motor that is connected to two contacts mounted in the housing and positioned to make contact with the terminals of the battery when the cartridge is received in the air flow inducing device.

8 Claims, 3 Drawing Figures

U.S. Patent  Nov. 9, 1976  3,990,848
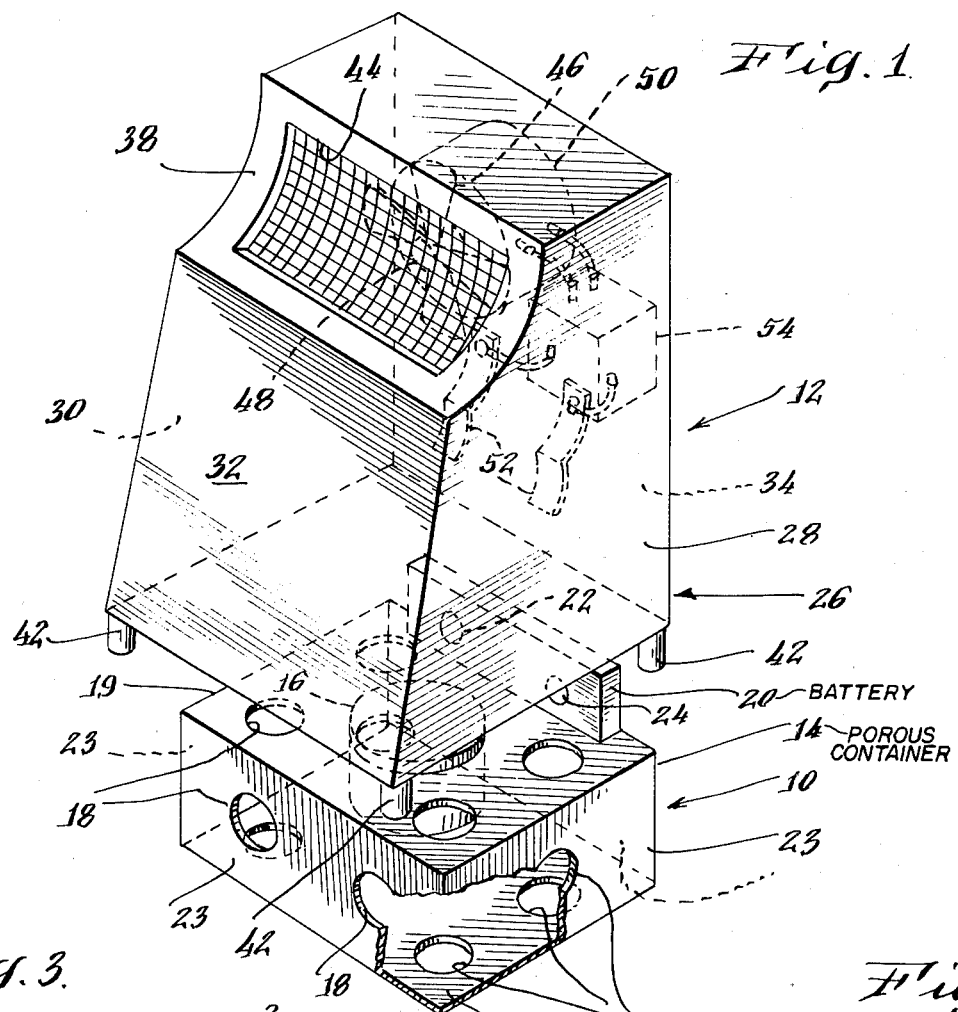
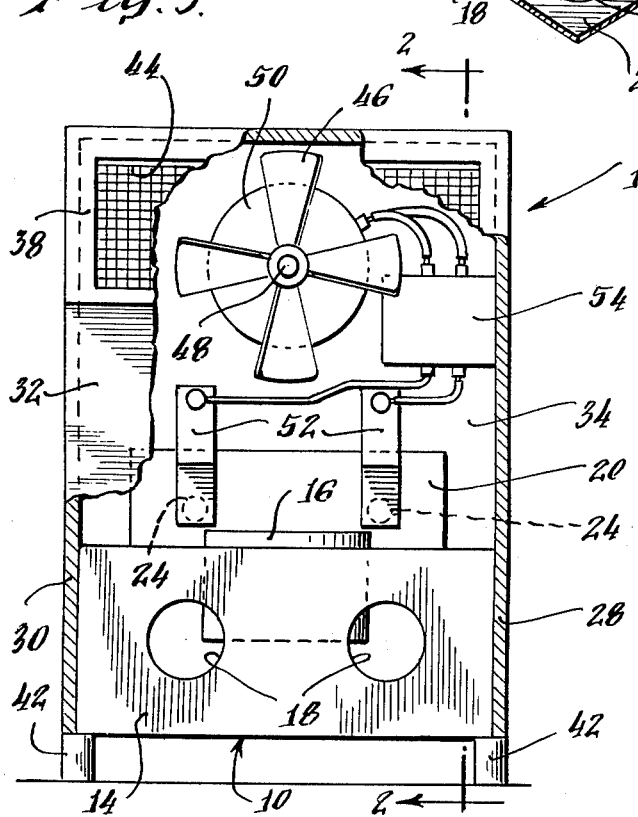
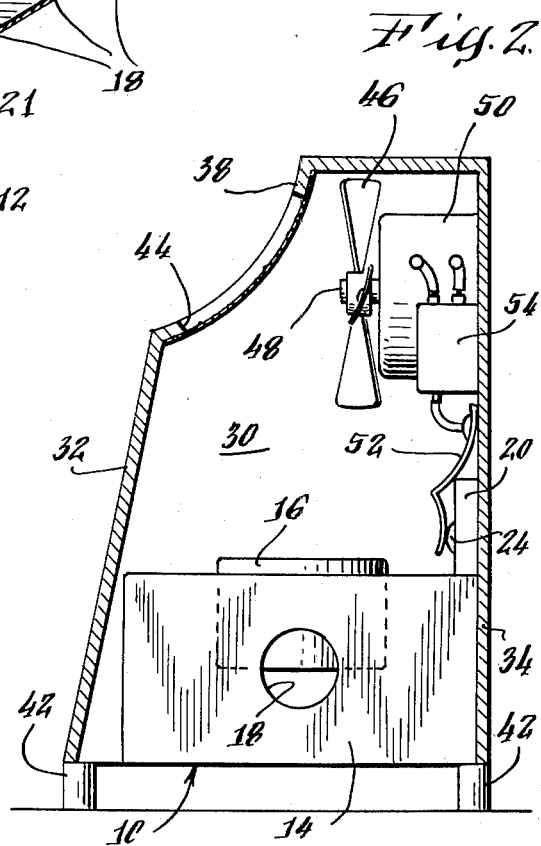

SYSTEM FOR INDUCING AIR FLOW PAST A GEL TYPE PRODUCT

BACKGROUND OF THE INVENTION

The present invention relates to a system for inducing air flow past a gel type product to aid distribution of the product, in vaporized form, into the environment.

Many products such as room deodorizers, insecticides, germicides, and the like are now manufactured in gel form. These products are continuously released into the environment in which they are exposed, be it open or enclosed, by evaporation and/or sublimation of the gel. Moreover, gel type products like room deodorizers are now usually used merely by exposing them in the environment to be treated.

However, depending on the intended application, it may be desirable to have even more distribution of the vaporized product throughout the environment than is possible by merely exposing the gel at a fixed location.

SUMMARY OF THE INVENTION

In a preferred embodiment to be described below in detail, the system of the present invention operates to induce air flow past a gel type product to aid in distribution of the product, in vaporized form, throughout the environment in which the system is installed. The system comprises a cartridge that includes a porous container for holding the gel type product and a battery mounted with the container.

The cartridge is shaped and sized to be received in an air flow inducing device that includes a housing having an air admitting opening and an air discharging opening. A fan is mounted in the housing to induce air flow successively through the air admitting opening, through the porous container, past the gel type product, and out of the air discharging opening into the environment. A motor is also mounted in the housing for driving the fan. Two contacts are located in the housing to contact the terminals of the battery when the cartridge is received in the air flow inducing device. Further, these contacts hold the cartridge firmly in the housing during the operation of the system.

The system of the present invention may advantageously include a timing circuit for automatically and periodically actuating the motor to automatically and periodically drive the fan.

The present invention is mechanically simple and may be practiced with inexpensive materials and components. Further, since the system is battery operated, it is completely portable and may be used indoors or out without regard to the availability of alternating current.

In the preferred embodiment, the cartridge is disposable. When the gel type product has been exhausted, the used cartridge is removed from the air flow inducing device and a new cartridge is inserted. Thus, the air flow inducing device may repeatedly be reused.

Accordingly, it is an object of the present invention to provide an inexpensive, uncomplicated, and portable apparatus for inducing air flow past a gel type product to aid distribution of the product throughout the environment.

Other objects, aspects, and advantages of the present invention will be pointed out in, or will be understood from, the following detailed description considered together with the accompanying drawings.

BRIEF DESCRIPTION OF THE DRAWINGS

FIG. 1 is a perspective view of the system of the present invention illustrating the cartridge prior to being inserted into the device for inducing air flow past the gel type product;

FIG. 2 is a side, vertical cross-sectional view of this system showing the cartridge installed in the air flow inducing device; and FIG. 3 is a front elevational view partly broken away to show detail of this system also illustrating the cartridge installed in the device for inducing air flow.

DETAILED DESCRIPTION OF THE PREFERRED EMBODIMENT

As illustrated in FIG. 1, the system of the present invention includes a cartridge, generally indicated at 10, and a device, generally indicated at 12, for inducing air flow past a gel type product to aid distribution of the product, in vaporized form, throughout the environment in which the system is installed.

The cartridge 10 includes a container 14 in which a solid, cylindrical block 16 of gel type product is mounted. Container 14 has a number of holes 18 in its top 19, bottom 21, and side walls 23 which facilitate flow of air around the block 16. Thus, by virtue of holes 18, container 14 is porous.

The cartridge 10 also includes a thin, rectangular battery 20, mounted with and upstanding from one side wall 23 of container 14, having two exposed terminals 22 and 24. This battery is of a type that is commercially available from, for example, Ray-O-Vac Division of ESB, Inc.

The device 12 for inducing air flow past the gel type product includes a housing 26 having two side walls 28 and 30, a front wall 32, a back wall 34, a top wall 36, and an arcuate grill front 38 which joins front wall 3 and top wall 36. Grill front 38 is formed with an open grill 44 that defines an air discharging opening. Moreover, housing 26 defines a cavity 40, open at the bottom to receive cartridge 10. Four feet 42 mounted at the corners of the housing walls elevate the bottom edges of these walls so that the open housing bottom forms an air admitting opening.

Device 12 further includes a fan 46 mounted on the shaft 48 of a motor 50 attached to the inside of back wall 34. Fan 46 is positioned in the upper part of the housing 26 to direct air through grill 44.

As shown in detail in FIGS. 2 and 3, two leaf-spring contacts 52 are also mounted on back wall 34 of housing 26. Each contact 52 is positioned to make contact with one battery terminal 22 and 24 when cartridge 10 is inserted into the cavity 40.

As shown in FIGS. 2 and 3, leaf-spring contacts 52 also clamp battery 20 against the inside of back wall 34 and thus operate to firmly hold cartridge 10 in device 12.

The contacts 52 are, in turn, connected to a timing circuit 54 which may be of the type described in U.S. Pat. No. 3,739,944 (Rogerson). This circuit, which is also connected to the motor 50, operates to automatically and periodically turn motor 50 on to automatically and periodically drive fan 46. Accordingly, when cartridge 10 is inserted into device 12, the fan automatically and periodically operates to induce air flow through the air admitting opening, namely the bottom of housing 26, through holes 18 in container 14, past the gel type product 16, and out through the grill 44.

As shown in detail in FIGS. 2 and 3, container 14 is shaped and dimensioned to snugly fit inside housing 26. Accordingly, most air is forced around gel type product 16 inside the container rather than by-passing the container.

Cartridge 10 is disposable. That is, when gel type product 16 has been exhausted through evaporation and/or sublimation, cartridge 10 is removed from the device 12 and discarded. A new cartridge may then be inserted into device 12 for subsequent use.

The system of the present invention provides a simple yet effective means for inducing air flow past the gel type product to evenly distribute the product, when vaporized, throughout the environment in which the system is installed. Further, since the fan is battery operated, the system is completely portable and may be used in any desired environment.

Although a preferred embodiment of the present invention has been described above in detail, it is to be understood that this is for purposes of illustration. Modifications can be made by those skilled in the art in order to adapt this system for inducing air flow past a gel type product and into the environment to particular applications.

What is claimed is:

1. A system for inducing air flow past a product, capable of being vaporized, to release the product in vapor form into the environment, said system comprising:
   A. a self-contained, replaceable and disposable cartridge including
      1. a quantity of a product which is capable of being vaporized;
      2. porous container means for holding and exposing the product to air flow, and
      3. a battery mounted with and attached to said container means; and
   B. air flow inducing apparatus including
      1. a housing defining
         a. a cavity shaped and sized to receive said cartridge,
         b. an access opening through which said cartridge may be inserted into said cavity,
         c. an air admitting opening,
         d. an air discharging opening, and
         e. an air flow path leading successively from the air admitting opening, through the cavity, and out of the air discharging opening,
      2. fan means mounted in said housing to induce air flow along said air flow path and through said container means past the product when said cartridge is received in said cavity,
      3. battery powered motor means for driving said fan means, and
      4. contact means mounted in said housing, exposed in said cavity, and electrically connected to said motor means for contacting and electrically connecting said battery to said motor means when said cartridge is received in said cavity.

2. The system for inducing air flow past a product, capable of being vaporized, to release the product in vapor form into the environment as claimed in claim 1 further comprising:
   timer means electrically connected between said contact means and said motor means for automatically and periodically providing power to said motor means from said battery to automatically and periodically drive said fan.

3. The system for inducing air flow past a product, capable of being vaporized, to release the product in vapor form into the environment as claimed in claim 1 wherein said housing air admitting opening is said access opening through which said cartridge may be inserted into said cavity.

4. The system for inducing air flow past a product, capable of being vaporized, to release the product in vapor form into the environment as claimed in claim 1 wherein said cartridge container means comprises:
   a hollow container for holding the product, said container having bottom, top and side walls, each of at least said top and bottom walls defining at least one hold to provide an air flow passage through said container past the product.

5. The system for inducing air flow past a product, capable of being vaporized, to release the product in vapor form into the environment as claimed in claim 1 wherein said cavity is shaped and sized to snugly receive said cartridge to force substantially all air flow induced along said air flow path to be conducted through said container past the product.

6. In a system including an apparatus for inducing air flow past a product, capable of being vaporized, to release the product in vapor form into the environment, the apparatus including a housing defining a cartridge receiving cavity, fan means mounted in the housing to induce air flow through the cartridge receiving cavity and out of the housing, motor means for driving the fan means, and contact means, electrically connected to the motor means, mounted in the housing for contacting and electrically connecting a supply of electrical power to the motor means; a self-contained, replaceable and disposable cartridge adapted to cooperate with the apparatus, said cartridge comprising:
   A. a quantity of a product which is capable of being vaporized,
   B. porous container means for holding and exposing the product to air flow, and
   C. a battery mounted with and attached to said container means, said battery and container means being shaped and sized to be received in the cartridge receiving cavity, said battery having terminals positioned to make electrical contact with the contact means when said container and battery are received in the cartridge receiving cavity whereby, when so received, said battery powers the motor means to drive the fan means and induce air flow past said quantity of product held and exposed in said container.

7. The self-contained, replaceable and disposable cartridge as claimed in claim 6 wherein said porous container means comprises:
   a hollow container for holding the product, said container having bottom, top and side walls, each of at least said top and bottom walls defining at least one hole for providing an air flow passage through said container past the product.

8. The self-contained replaceable and disposable cartridge as claimed in claim 6 wherein said container means and battery are shaped and sized to snugly fit into the cartridge receiving cavity to force substantially all air flow induced through the cavity to be conducted through said container means past the product.

* * * * *